(12) United States Patent
Branch et al.

(10) Patent No.: US 7,537,616 B1
(45) Date of Patent: May 26, 2009

(54) IMPACTED ORTHOPEDIC BONE SUPPORT IMPLANT

(75) Inventors: Charles L. Branch, Advance, NC (US); John L. White, Bartlett, TN (US); Bradley T. Estes, Durham, NC (US); Eddie Ray, III, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 103 days.

(21) Appl. No.: 10/312,174

(22) PCT Filed: Oct. 20, 2000

(86) PCT No.: PCT/US00/41392

§ 371 (c)(1),
(2), (4) Date: May 9, 2003

(87) PCT Pub. No.: WO01/28461

PCT Pub. Date: Apr. 26, 2001

Related U.S. Application Data

(60) Provisional application No. 60/160,506, filed on Oct. 20, 1999.

(51) Int. Cl.
*A61F 2/44* (2006.01)

(52) U.S. Cl. .................. 623/17.16; 623/17.11

(58) Field of Classification Search ... 623/17.11–17.16, 623/23.26, 23.33, 23.44; 606/70, 74
See application file for complete search history.

(56) References Cited

U.S. PATENT DOCUMENTS

| | | | | |
|---|---|---|---|---|
| 3,720,959 A | | 3/1973 | Hahn | |
| 4,820,305 A | * | 4/1989 | Harms et al. | 623/16.11 |
| 5,562,736 A | * | 10/1996 | Ray et al. | 606/86 A |
| 5,609,635 A | * | 3/1997 | Michelson | 623/17.16 |
| 5,643,314 A | * | 7/1997 | Carpenter et al. | 623/1.2 |
| 5,702,451 A | * | 12/1997 | Biedermann et al. | 623/17.16 |
| 5,897,556 A | | 4/1999 | Drewry | |
| 6,086,613 A | * | 7/2000 | Camino et al. | 623/17.16 |
| 6,123,705 A | * | 9/2000 | Michelson | 623/17.16 |
| 6,258,125 B1 | * | 7/2001 | Paul et al. | 623/17.11 |
| 6,972,035 B2 | * | 12/2005 | Michelson | 623/17.11 |
| 7,238,203 B2 | * | 7/2007 | Bagga et al. | 623/17.11 |
| 7,285,135 B2 | * | 10/2007 | McKay et al. | 623/17.16 |
| 7,396,365 B2 | * | 7/2008 | Michelson | 623/17.11 |
| 2007/0010885 A1 | * | 1/2007 | Liu et al. | 623/17.11 |
| 2007/0106388 A1 | * | 5/2007 | Michelson | 623/17.16 |
| 2007/0203497 A1 | * | 8/2007 | Zucherman et al. | 606/61 |
| 2008/0103602 A1 | * | 5/2008 | Berry et al. | 623/17.16 |

FOREIGN PATENT DOCUMENTS

| | | | |
|---|---|---|---|
| EP | 0369603 | * | 5/1990 |
| FR | 2 710 519 | | 4/1995 |
| WO | WO 98 26725 | | 6/1998 |

* cited by examiner

*Primary Examiner*—Paul Prebilic

(57) ABSTRACT

This invention relates to a porous bone implant (10, 110, and 210), a method of manufacturing the implant and a method of orthopedic treatment. The mesh implant can be manufactured using extrusion techniques and a variety of cutting and machining processes to provide the implant with the desired structural features and in the required dimensions to be matingly received within the bone defect or cavity. The implant can be used to strengthen bone structures and support bone tissue adjacent to a defect of cavity. Thus, the implant can be used to provide improved treatment of patients having bone defects or diseases with decreased postoperative pain and a shorter recovery time.

37 Claims, 6 Drawing Sheets

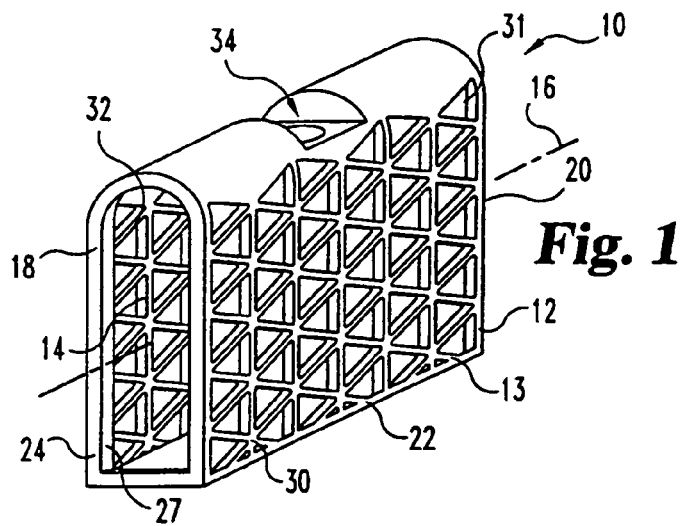
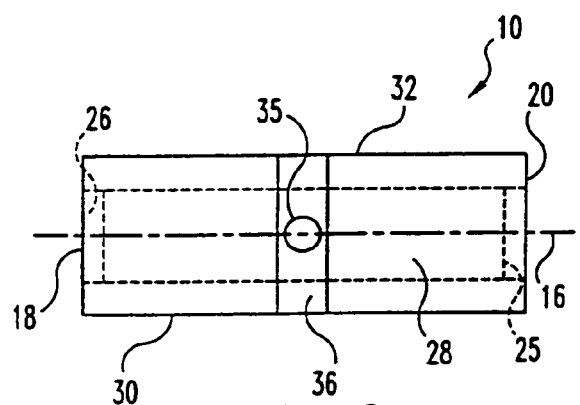
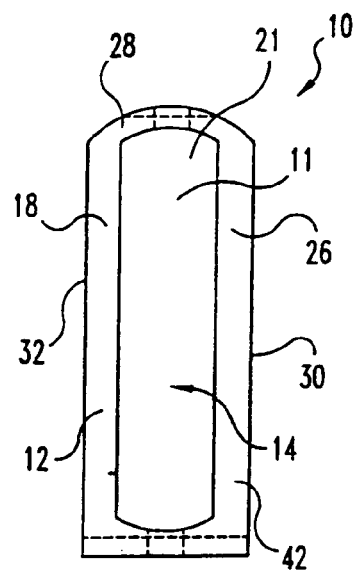
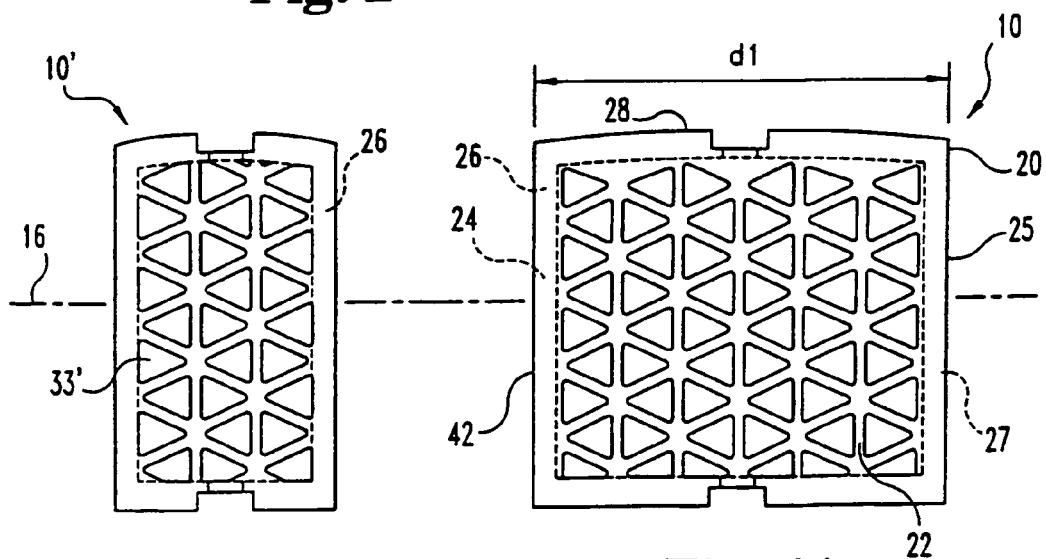
Fig. 1
Fig. 2
Fig. 3
Fig. 4B
Fig. 4A

IMPACTED ORTHOPEDIC BONE SUPPORT IMPLANT

CROSS-REFERENCE TO RELATED APPLICATION

The present application claims the benefit of U.S. Provisional Application Ser. No. 60/160,506 filed on Oct. 20, 1999, and entitled "Impacted Orthopedic Bone Implant," which is hereby incorporated by reference in its entirety.

BACKGROUND OF THE INVENTION

The present invention concerns a device for implantation into bone tissues, a method of manufacturing such a device, and a method of orthopedic treatment. More specifically, this invention is directed to an orthopedic mesh implant for implantation into bone cavities to support bone tissue adjacent to the cavity. The invention is also specifically directed to methods of manufacturing a mesh implant and to methods for treating patients using the mesh implant.

The repair and reconstruction of bone structures having a defect, such as a cavity, crack or chip, can be accomplished by directly fixing bone structures adjacent a defect to each other, such as by plate(s) and screw(s). In other instances an osteogenic material, i.e. a bone growth inducing material, can be introduced into the bone defect to promote bone growth to fuse the bone structures together. Implantation of bone growth material can be particularly advantageous where the bone includes a cavity because a portion of the bone structure or adjoining structure is missing. Cavities can be formed naturally, by trauma, or because of intentional harvesting of bone grafts for implantation into other bone structures.

While implants are known that may provide stability between adjacent bony structures, the effectiveness, as well as the cost of manufacture and availability of such implants, limits the advantages that may be realized.

A cylindrical spacer assembly is described in WO 99/32055. The spacer assembly includes opposite, detachable endcaps that connect with the spacer body with interdigitating teeth.

In light of the above-described problems, there is a continuing need for advancements in devices and methods relating to orthopedic treatment of bone defects and diseases to reduce the treatment risks and enhance the patency bone fusion devices. The present invention is such an advancement and provides a wide variety of benefits and advantages.

SUMMARY OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

According to one form of the invention, there is provided an implant for insertion into bone structures. The implant comprises a hollow body having an interior chamber, a first and second end for bearing against bone tissue and each end having an opening providing communication with the interior chamber. The hollow body is formed to include one or more mesh sides having a grid work of openings into the interior chamber. Thus, the invention provides a device that is implantable into bone structures and provides a depot for deposition of bone growth inducing material to promote bone growth and to provide support for weak bone structures.

In another form, the invention provides an implant for supporting weak bone tissue. The implant comprises a mesh body having an interior chamber and a passageway therethrough and defining a longitudinal axis substantially parallel to the passageway; the body includes a first end and a second end, each end positioned substantially transverse to the longitudinal axis and each end having a supporting portion positioned about the perimeter of the respective ends. The mesh body also includes a central portion having a longitudinal wall extending from the first end to the second end and having formed therein a grid work of openings providing communication into the interior chamber. In preferred embodiments, the supporting portions include an uninterrupted support band positioned about the periphery of each of the first and second end. In other preferred embodiments, the implant includes at least one tool-engaging portion provided in the longitudinal wall. In still other preferred embodiments, the implant is formed as a one-piece unitary body.

It is one object of the present invention to provide an orthopedic bone support implant to facilitate reconstruction and/or repair of bone structures.

Further objects, features, aspects, forms, advantages and benefits shall become apparent from the description and drawings contained herein.

BRIEF DESCRIPTION OF THE DRAWINGS

FIG. 1 is a perspective view of one embodiment of an implant according to the present invention.

FIG. 2 is a top plan view in partial section of the implant depicted in FIG. 1.

FIG. 3 is an end elevation view in partial section of the implant depicted in FIG. 1.

FIG. 4A is a side elevation view in partial section of the implant depicted in FIG. 1.

FIG. 4B is a side elevation view in partial section of an implant similar in configuration to the implant depicted in FIG. 1, but having a shorter length.

DETAILED DESCRIPTION OF THE INVENTION

Figure 5:
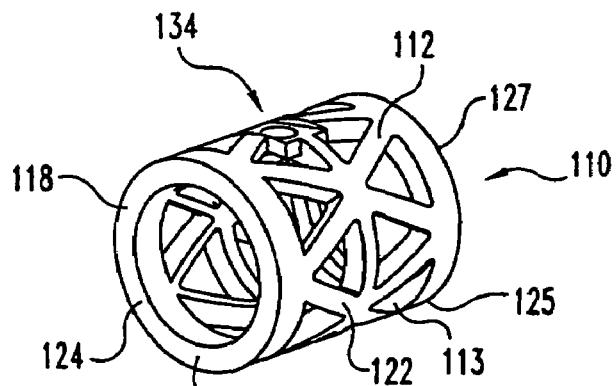
FIG. 5 is a perspective view of one embodiment of a cylindrical implant according to the present invention.

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

The present invention contemplates an implant for insertion into bone structures. In one aspect of the invention, the implant provides a device for supporting weak bone structures. In other aspects, the implant provides a receptacle for deposition of bone growth material. In still other aspects the implant of this invention is intended to replace current mesh or cage-type devices for engagement with bone structures. The implant of this invention is provided to be implanted into bone structures. The phrase "implanted into bone structures" is not intended to limit this invention to implantation into a single bone structure. Therefore, it is also within the scope of this invention to provide implants that can be implanted between adjacent bone structures, for example, in an intervertebral space between adjacent vertebrae.

FIGS. 1-4A and 4B illustrate one embodiment of a mesh bone implant 10 according to the present invention. Bone implant 10 includes a body 12 having an interior chamber 11. Implant 10 also includes a first end 18 and opposite second end 20 and a central portion 22 extending from first end 18 to second end 20. Central portion 22 includes a first longitudinal wall 13 having a first longitudinal wall portion 30 and a second longitudinal wall portion 32 and passageway 14 therethrough defining a longitudinal axis 16.

First end 18 includes a support portion 24 positioned about its perimeter. In one form, support portion 24 includes an integrally formed support band 26 positioned circumferentially about longitudinal axis 16. Band 26 is adapted to withstand impaction forces to seat impact implant 10 into a defect or a prepared cavity in the bone structure. In one form, band 26 is an uninterrupted band having an outer peripheral surface flush with the exterior surface of the longitudinal wall 13, and can be provided as an integrally formed band having a cross section thicker than the cross section of other wall portions, i.e. walls 30 and 32, of body 10. Preferably, band 26 does not extend beyond either wall 30 or wall 32 in a direction orthogonal to and away from longitudinal axis 16. In this form, wall portions 30 and 32 define a substantially planar surface extending from first end 18 to second end 20. Band 26 can taper uniformly in a direction towards interior chamber 11; gradually increasing in width to a maximum width proximate to first end 18. Extension of band 26 internally serves to provide a thickened portion to enhance the load bearing capabilities of implant 10. Further, internal projections of band also provide a retaining ring about the perimeter of first end 18. Ring 27 provides containment of osteogenic material deposited in internal chamber 11 and facilitates greater packing density of the osteogenic material by inhibiting the escape of the packed osteogenic material from the implant. In other forms, band 26 can be provided as a lip or abutment extending from the perimeter of first end 18 toward the interior chamber proximate to first end 18.

Figure 14:
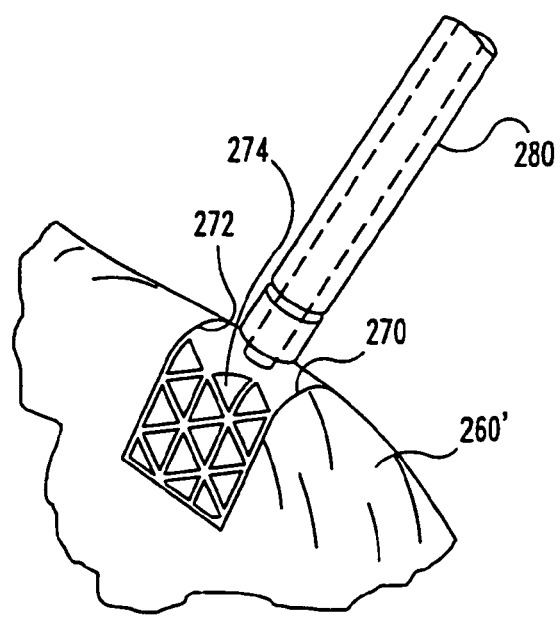
FIG. 14 is an illustration of impacting an implant of the present invention into bone tissue.

Band 26 includes an exterior bearing surface 42. Preferably, first surface 42 defines a substantially planar surface positioned substantially to lie in a plane generally perpendicular to longitudinal axis 16. Further, first surface 42 is adapted to engage an adjacent facing surface of a bone defect or bone cavity. In one form, the first surface is a roughened or knurled surface to secure implant 10 to the adjacent bone surfaces. First end 18 also includes an opening 21 into interior chamber 11. In the preferred form of the illustrated embodiment in FIG. 14, interior perimeter of band 26 defines opening 21.

Second end 20 is opposite central portion 22 from first end 18. Second end 20 includes a second support portion 25. Second support portion 25 can be provided as is substantially described for first support portion 24 and can include a second support band 27. Further, second end 20 also includes an opening into interior cavity 11 as described for first end 18.

In one embodiment, first end 18 and second end 20 are separated by a distance, d1. Distance d1 is selected so that implant 10 is matingly received within a cavity or other defect in a bone structure. When d1 is properly selected, first end 18 and second end 20 each can bear against respective facing bone tissue of a cavity or other defect and provide support and strength to the bone structure. As an example of implants having varying d1 distances, an implant similar in configuration to implant 10 is illustrated in FIG. 4B. Implant 10' is selected to have a shorter longitudinal length, d1, implant 10.

It is also intended to include within the scope of this invention a series of implants, each having a configuration as described for implant 10, but differing in length d1.

Central portion 22 extends from first end 18 to second end 20 and includes a longitudinal wall 13. Longitudinal wall 13 includes a plurality of openings 31 providing communication with the interior chamber 11. In one form, the plurality of openings 31 define a grid pattern or grid work on first wall 30. Each of the plurality of openings 31 can be formed in a variety of configurations, including triangular, square, rectangular, and polyhedron. In a preferred form, the intersecting bars define a pattern of equilateral triangles or isosceles triangles. In another form, the gridwork or grid pattern is formed by a plurality of intersecting elongate bars. In a preferred form, the plurality of intersecting elongate bars include a first group of elongate bars have a longitudinal bar axis arranged perpendicular to longitudinal axis 16 and a second group of elongate bars having a longitudinal bar axis arranged non-perpendicular relative to longitudinal axis 16. A plurality of joints are formed by the intersections of the elongate bars, each joint defining a corner of an opening into interior chamber 11.

The elongate bars can define a repeating pattern of triangles on wall sections 30 and 32, preferably isosceles triangles; more preferably, equilateral triangles. When equilateral triangles are used, the wall portions can have a maximum amount of open areas, while still retaining the requisite strength to support adjacent bone structures. The trim open area is intended to mean the sum of the area of the plurality of open portions 31 in walls portions 30 and 32, respectively.

Preferably, the ratio of open area to the total surface area defined by either wall portion 30 (or wall portions 32) is greater than about 1:2; more preferably greater than about 3:4. That is, at least 50% of the exterior surface area of either wall portion 30 or 32 is open area Longitudinal wall 13 can include a first wall section 30 and an opposing second wall section 32. First wall 30 extends from first end 18 to second end 20 and defines a plane that is substantially parallel with longitudinal axis 16. Second wall 32, similar to first wall 30, extends from first end 18 to second end 20 and defines a plane that is also substantially parallel with longitudinal axis 16. Thus in one form, first wall portion 30 and second wall portion 32 are positioned to lie substantial parallel to each other.

Longitudinal wall 13 also includes a tool insertion end 28. Tool insertion end 28 is positioned substantially orthogonal to first wall portion 30 and extends in a direction substantially parallel to longitudinal axis 16. Tool insertion end 28 includes the tool-engaging portion 34. Tool-engaging portion 34 can be provided in a variety of features adapted to engage an insertion tool for insertion of implant 10 into a prepared bone tissue. For example, tool-engaging portion 34 can include a variety of indents and openings, which may or may not be threaded, to engage corresponding configured features on an insertion manipulation accessory (not shown) to facilitate implantation of implant 10 into bone tissue. In a preferred embodiment of FIG. 14, tool-engaging portion 34 includes a longitudinally extending threaded bore 35 and a driving indent 36.

Tool insertion end 28 defines an exterior surface 37. In one form, surface 35 is curved in a direction transverse to longitudinal axis 16 from wall portion 30 to wall portion 32. In another form, the exterior surface defines an arcuate surface in a direction along axis 16 and extending from the first end.

Figure 6:
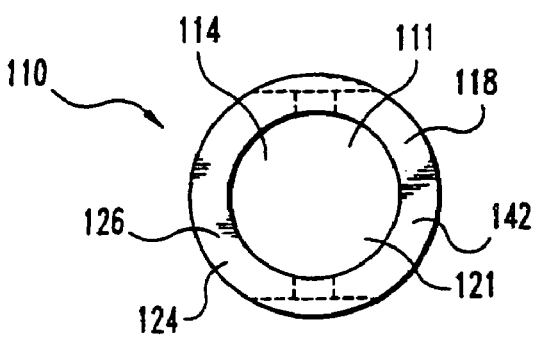
FIG. 6 is an end elevation view in partial section of the implant depicted in FIG. 5.
Figure 7:
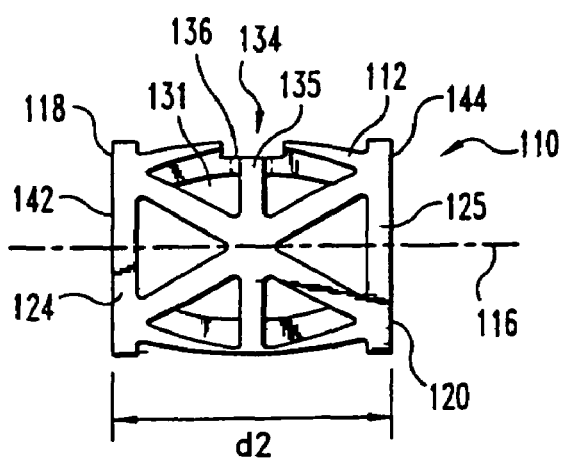
FIG. 7 is side elevation view in partial section of the implant depicted in FIG. 5.

Referring now to FIGS. 5-7, there is depicted another embodiment of a mesh bone implant according to the present invention for supporting bone structures. In the preferred form of the illustrated embodiment, mesh implant 110 includes a cylindrical body 112 having a mesh wall 113 defining an interior chamber 111 therein. Body 112 includes a passageway 114 therethrough defining a longitudinal axis 116. Preferably, cylindrical wall 113 extends circumferentially about longitudinal axis 116. In the illustrated embodiment, cylindrical wall 113 is formed in the shape of a cylinder. However, it is understood that the mesh wall 113 can define a variety of shapes, including shapes having at least one flat surface.

Body 112 includes a first end 118 and an opposite second end 120. First end 118 and second end 120 each include a support portion 124 and 125, respectively. In one form, support portions 124 and 125 each include a support band, 126 and 127 respectively, positioned circumferentially about longitudinal axis 116. Support bands 126 and 127 can be provided as an uninterrupted band about the perimeter of first end 118 and second end 120, respectively. Support band 126 includes an exterior surface 142 that is provided as a substantially smooth surface and defining a plane generally transverse to longitudinal axis 116. Similarly, support band 127 includes an exterior surface 144 that is provided as a substantially smooth surface and defining a plane generally transverse to longitudinal axis 116. The substantially smooth planar surfaces 142 and 144 of support band 126 and 127, respectively, facilitate implantation of implant 110 into bone structures. These surfaces provide particular advantages when implant 110 is inserted into a prepared cavity in a bone structure and engage the walls of the cavity to provide additional support to the bone structure.

Support portions 124 and 125 are provided to withstand the requisite impulsion force to seat implant 110 into a bone defect or a prepared cavity. The support portions 124, 125 can be formed from wall section having a thicker cross section then other wall sections of body 112. Thus, the support bands 124 and 125 can be provided in a form as described above for support portions 24 and 25.

First end 118 and second end 120 are separated by a distance, d2. Distance d2 is selected so that implant 110 is matingly received within a prepared cavity or other defect in a bone structure. When d2 is properly selected, first end 118 and second end 120 each can bear against respective facing bone tissue of a cavity, bone defect or opposing faces of adjacent bone structures and provide additional strength to the bone structure(s).

First end 118 and second end 120 each include an opening, 121 into the interior chamber 111. Opening 121 provides communication with passageway 114 through body 112. In the preferred form of the illustrated embodiment in FIGS. 5-7, the interior perimeter of bands 126 and 127 each define an opening 121.

Mesh implant 110, similar to mesh implant 10, includes a central portion 122 extending from first end 118 to second end 120. In one aspect, cylindrical mesh wall 113 defines central portion 122. Cylindrical mesh wall 113 also includes a plurality of openings 131. Openings 131 can be provided in a variety of patterns, including triangular (equilateral or isosceles), square, rectangular, and polyhedron, thereby forming a mesh wall. Preferably, outer peripheral wall 130 includes a uniform grid of a plurality of openings 131. In another form, cylindrical mesh wall 113 can be formed by a plurality of intersecting elongate bars. The plurality of intersecting elongate bars include a first group of elongate bars have a longitudinal bar axis arranged perpendicular to longitudinal axis 116 and a second group of elongate bars having a longitudinal bar axis arranged non-perpendicular relative to longitudinal axis 116. A plurality of joints are formed by the intersections of the elongate bars of the first and second groups, each joint forming an apex that defines a corner of one of the openings of the plurality of openings 131 into interior chamber 111. In another form, cylindrical wall 113 is defined by a plurality of intersecting elongate bars including a first group of bars defining a plane perpendicular to longitudinal axis 116. A second group of bars having an elongate axis arranged non-perpendicular to longitudinal axis 116 intersects the bars in the first group of bars. Again, a plurality of apexes are formed by the intersection of the first group of bars and the second group of bars. The apexes form one of the corners of the openings 131 in cylindrical wall 113. Cylindrical wall 113 can be provided substantially as described for wall 13.

Cylindrical wall 113 includes a tool engagement portion 134. Tool engagement portion 134 can be provided as described for tool engagement portion 34, and can include a threaded bore 135 and a driving indent 136.

Figure 8:
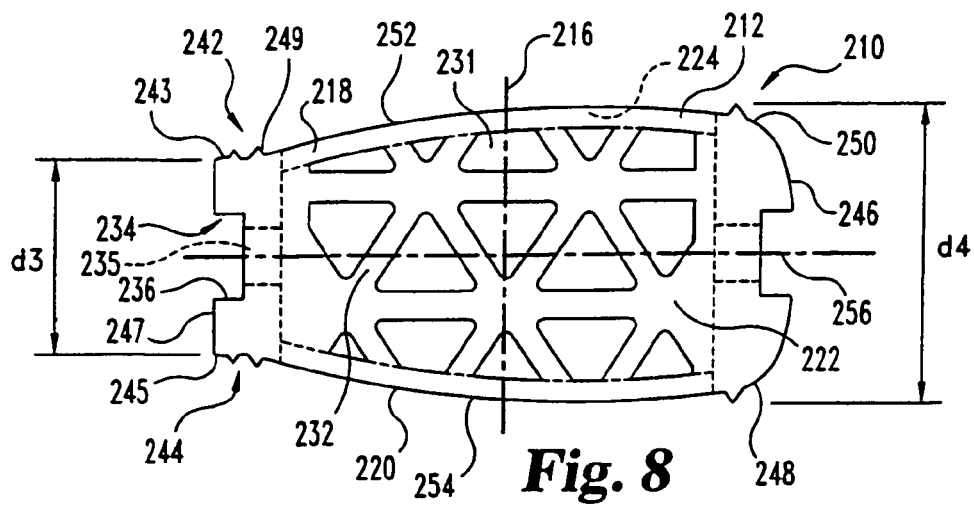
FIG. 8 is a side elevation view in partial section of an alternative embodiment of an implant according to the present invention.
Figure 9:
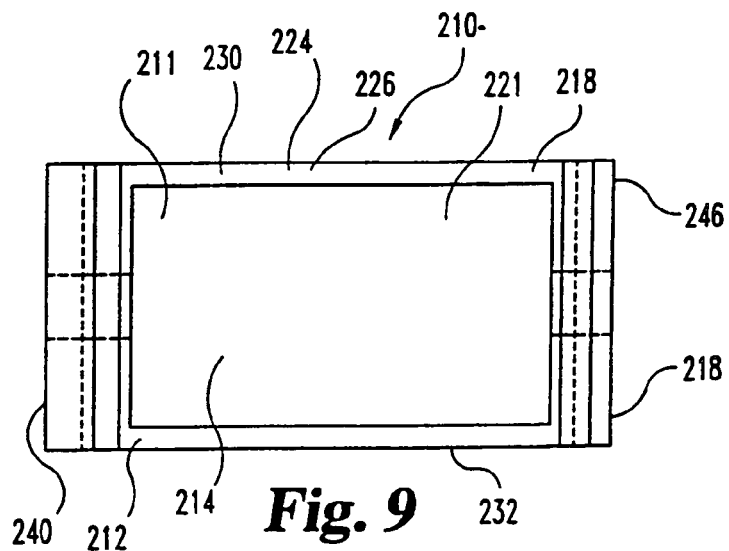
FIG. 9 is a top elevation view in partial section of the implant depicted in FIG. 8.
Figure 10:
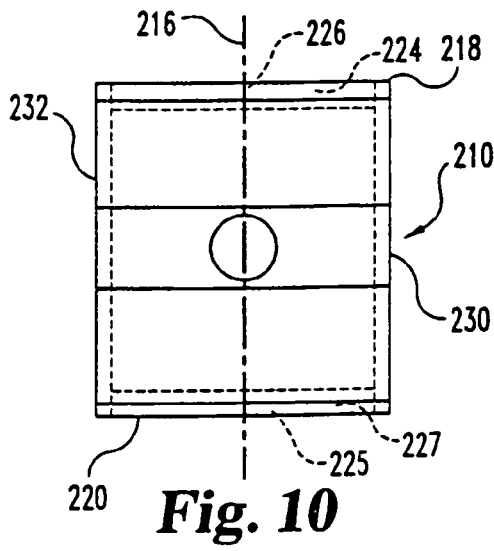
FIG. 10 is an end elevation view in partial section of the implant depicted in FIG. 8.
Figure 11:
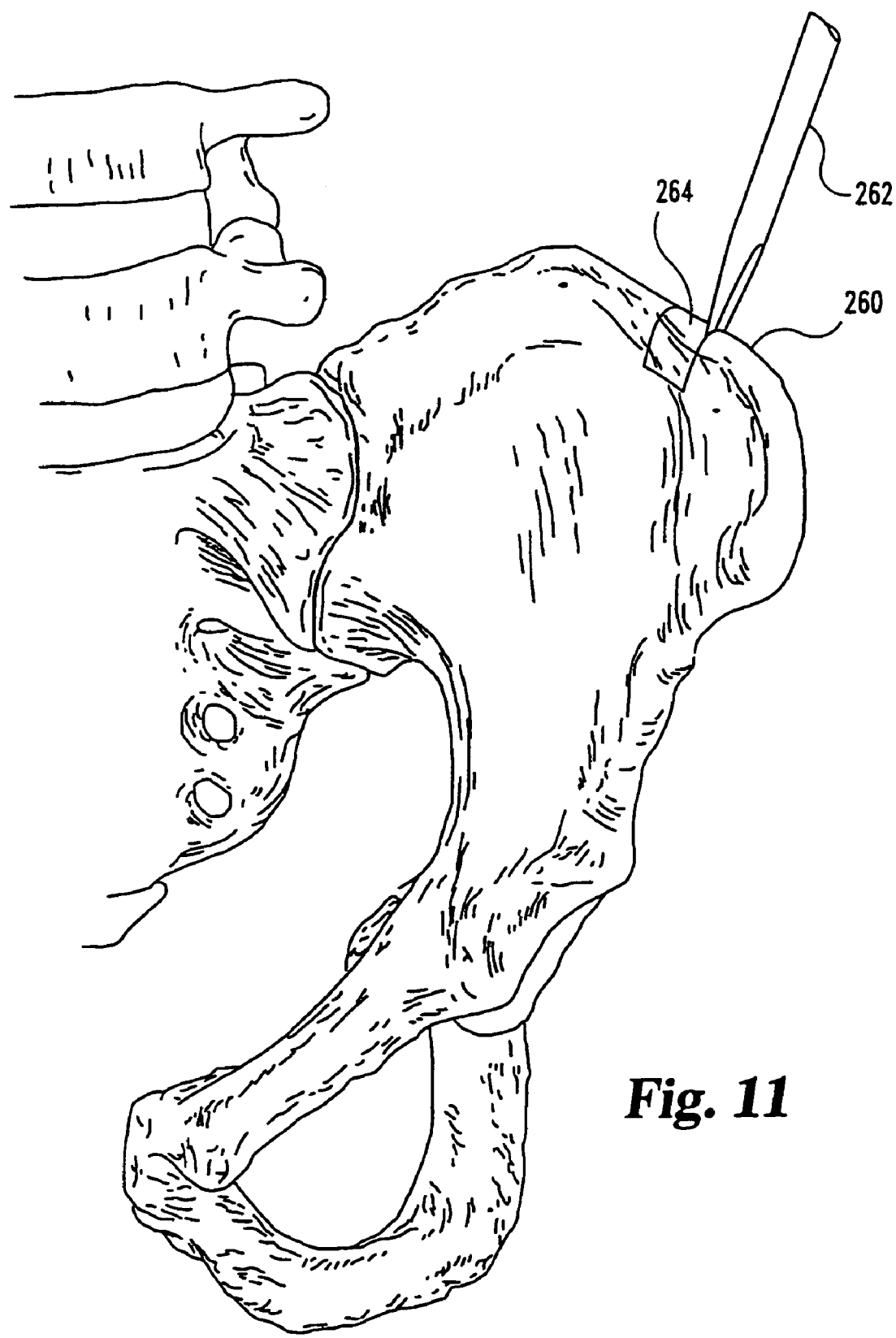
FIG. 11 is an illustration of cutting a bone graft from the iliac crest.

Another form of the invention is illustrated in FIGS. 8-10. Mesh implant 210 is depicted generally as a rectangular prism body 212 having a central portion 222 and an interior chamber 211 formed therein. Body 212 includes a passageway 214 therethrough defining a longitudinal axis 216. Body 212 includes a first transverse wall 240, an opposite second transverse wall 246, and a central portion 222 extending from first end 218 to second end 220.

First end 218 includes an opening 221 extending into interior chamber 211. Similarly, second end 220 includes a second opening extending into interior chamber 211. First end 218 also includes a support portion 224 extending about the perimeter of first end 218. Similarly, second end 220 includes support portion 225 extending about its perimeter. Support portions 224 and 225 each include a support band 226 and 227, respectively, positioned generally circumferentially about longitudinal axis 216. Bands 226 and 227 are adapted to withstand forces needed to impact implant 210 into a prepared cavity in a bone structure or between adjacent bone structures. In one form, bands 226 and 227 can be provided as integrally formed bands having a cross section thicker than the cross section of other wall portions, particularly mesh walls 230 and 232, of body 210. In other forms, band 226 (or 227) can be provided as an abutment or a lip extending from the perimeter of first end 218 (or second end 220) toward the interior chamber 211 substantially as has been described for bands 26, 27, 126 and 127.

In a preferred form of the illustrated embodiment of implant 210, first end 218 and second end 220 are provided as arcuate surfaces 252 and 254, respectively, along a transverse axis 256 positioned to be substantially orthogonal to longitudinal axis 216. Arcuate surfaces 252 and 254 each have a maximum height positioned between first transverse wall 240 and second transverse wall 246. In use, at least a portion of arcuate surfaces 252 and 254 can extend into bone tissue, such as cancellous tissue underlying the endplates of vertebral bodies. Arcuate surfaces 252 and 254 inhibit expulsion of the implant from the bone cavity by providing an implant that has a maximum height that is greater than height of a surgically prepared bone cavity, for example, in an intervertebral space between adjacent vertebrae.

Central portion 222 also includes first longitudinal wall 230 and second longitudinal wall 232. At least one, and preferably both, of longitudinal mesh walls 230 and 233 are positioned to define a plane that is generally parallel to longitudinal axis 216. Further, first wall 230 and second wall 232 are provided with a plurality of openings 231 into interior chamber 211. Preferably, first wall 230 and second wall 232 are provided with a pattern of substantially uniform apertures forming a mesh. The apertures can be provided in a variety of configurations, including circular, square, rectangular, polyhedron, and the like. A plurality of openings 231, similar to the openings 11 described for implant 10, can be formed into walls 230 and 232. In a preferred form, the apertures are provided in a form of an equilateral or isosceles triangle. Further, first wall 230 and second wall 232 can be defined by a plurality of intersecting elongate bars as described for cylindrical wall 113 for implant 110 and wall 13 of implant 10.

In one form, implant 210 can be inserted in a defect or a prepared cavity between two bone structures to provide support and strengthen the adjacent bone structures. Therefore, body 212 can include a first transverse wall 240 extending between first end 218 and second end 220 and positioned generally orthogonal to longitudinal wall 230, and an opposing transverse wall 246 also extending between first end 218 and second end 220 and positioned generally orthogonal to longitudinal wall 230. Transverse wall 240 can include a first bearing surface 242, an opposite second bearing surface 244, and a transverse face 247 therebetween. Preferably, first bearing surface 242 and second bearing surface 244 include substantially planar surfaces 243 and 245, respectively, adapted to engage adjacent surfaces of the prepared bone cavity or bone defect. When inserted into the prepared cavity or bone defect, at least one of first bearing surface 242 or second bearing surface 244 bear against the adjacent bone tissue.

In one embodiment, first bearing surface 242 and second bearing surface 244 are separated by a distance d3 selected to engage first bearing surface 242 and second bearing surface 244 with corresponding opposing adjacent bone structures in the prepared cavity or bone defect. Further, in a preferred aspect, first bearing surface 242 and second bearing surface 244 are substantially planar surfaces extending generally parallel to transverse axis 256.

First transverse wall 240 includes a tool-engaging portion 234. Tool-engaging portion 234 can be configured as described for tool-engaging portion 34 of implant 10, including a threaded bore 235 and driving indent 236.

In the preferred embodiments, first and/or second bearing surfaces 242 and 244 include anti-expulsion features 249, for example, ridges, teeth, and other projections, adapted to inhibit the expulsion of implant 210 from the prepared cavity or bone defect. In the preferred form, the anti-expulsion features are adapted to minimize the force needed to insert implant 210 into the prepared space or bone defect, yet inhibit expulsion of implant 210. Examples of such preferred forms include: at least one ridge transverse to longitudinal axis 216, a plurality of ridges, teeth, or spikes. In a preferred form, the anti-expulsion features are adapted to minimize the force needed to insert implant 210 into prepared intervertebral space, yet inhibit expulsion of implant 210. Examples of such preferred forms include ratchet-shaped ridges or teeth that have an apex pointing toward the first terminal end. When thus configured, the ratchet-shaped ridges or teeth chisel deeper into the cortical bone tissue in response to an expulsive force.

Body 212 also includes a second transverse wall 246 opposite the first bearing wall 240. Second transverse wall 246 can include a third bearing surface 248, an opposing fourth bearing surface 250, and a face extending therebetween. Third and fourth bearing surfaces 248 and 250, respectively, are separated by distance d4. In one preferred embodiment, distance d4 is selectively greater than distance d3 to conform to the desired prepared cavity in the bone structure, for example, in the intervertebral space between adjacent vertebrae. While third and fourth bearing surfaces 248 and 250 are shown as curved surfaces, it is understood that these bearing surfaces can be provided in a variety of shapes, including convex or ogival, in either the horizontal or vertical plane, or both, or substantially planar as depicted with the first and second bearing surfaces 242 and 244, respectively. Further, third and fourth bearing surfaces 248 and 250 can include anti-expulsion features as described for the first and second bearing surfaces 242 and 246.

Further, transverse wall 246 can include a tool-engaging portion as described for transverse wall 240, including a threaded bore and a driving indent.

Reference will now be made to use of mesh implants 10, 110, and 210 to support adjacent weak bony structures. Typically, mesh implants 10, 110, and 210 can be inserted into a bone structure after preparation of a suitable bone cavity. For example, implants can be inserted into the cavity resulting from harvesting an autograft from the iliac crest. Often, harvesting autografts leads to significant post-operative pain and lengthy recovery time. Use of the implants disclosed in this invention facilitates reconstruction of the cavity and accommodates a quicker recovery time, often with less pain to the patient.

Figure 12:
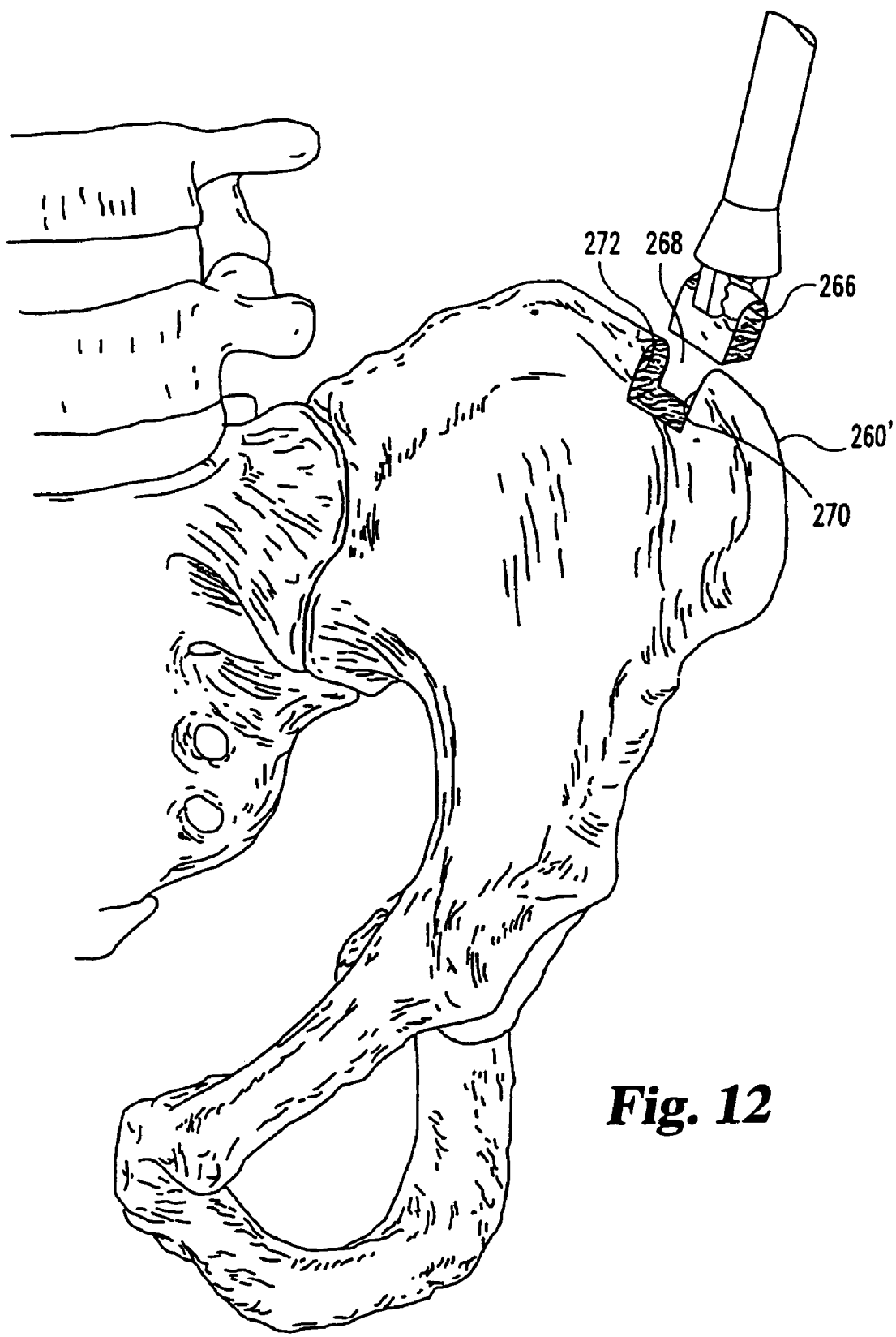
FIG. 12 is an illustration of harvesting the cut bone graft from the iliac crest.
Figure 13:
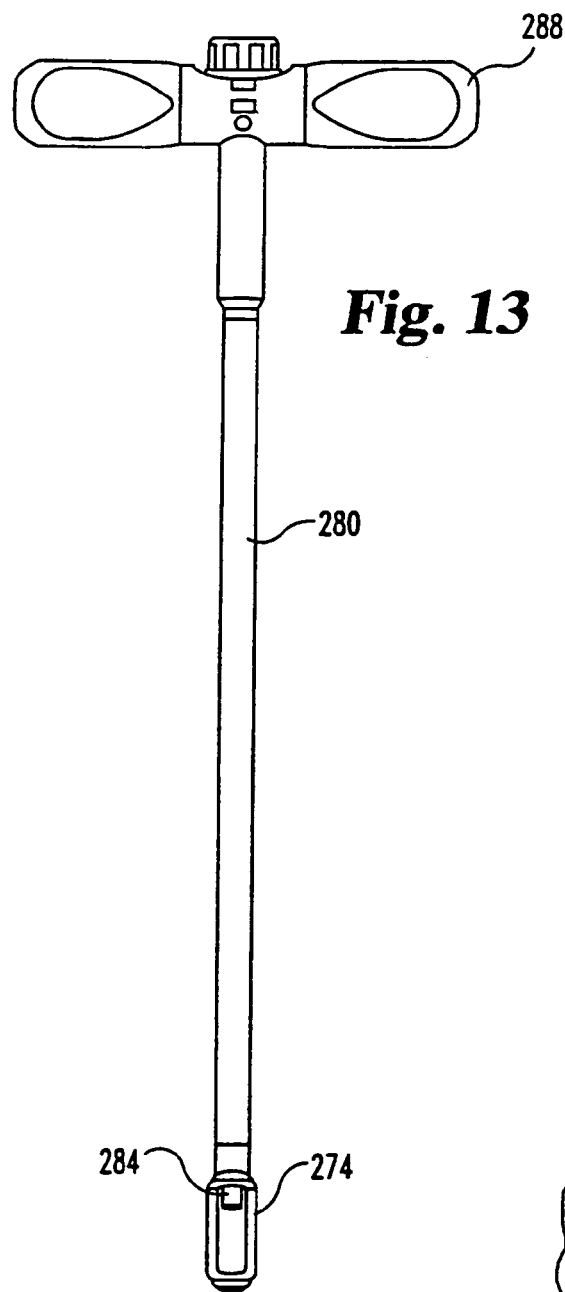
FIG. 13 is a side elevation view of an implant holder and an implant according to the present invention.

Referring now to FIGS. 11-14, a selected portion of the iliac crest 260 is removed using a surgical cutting device, such as, for example, a chisel 262, or a bone saw. After the selected region 264 of the iliac crest has been cut, the cut bone autograft 266 is removed from the residual bone structure 260' of the patient as depicted in FIG. 12. An implant as described in the present invention is selected for cavity 268 and to matingly engage in the adjacent bone structures 270 and 272, respectively. The selected implant 274 is releasably attached to an implant holder 280, preferably of a known variety. Preferably, implant holder 280 includes an implant insertion portion that is configured to matingly engage in tool-receiving portion 34, 134, and 234 of the selected implants. In preferred embodiments, the insertion portion includes a threaded shaft 284 to readily engage in a threaded bore in the implant. The implant insertion portion can also include a driving blade (not shown) to engage in a driving indent on the implant. In other embodiments, implant tool 280 can include a handle 288, which may or may not include an impaction tool, such as a slap hammer, to impact the implant into the prepared bone cavity or bone defect. Preferably, implants 10, 110, and 210 are made of a single, integral piece. The implants may be prepared from physiologically acceptable material having a requisite strength to withstand the compressive force exerted on the spinal column during normal activity. Examples of such acceptable material include: titanium, composites (carbon fiber or glass fiber composites), ceramics, bone, stainless steel, and surgical steel. Preferably, implants 10, 110, and 210 are prepared of metal such as titanium or surgical steel.

In the preferred manufacturing procedure, implants according to the present invention are made by an extrusion of a tube or hollow construct. The tube or hollow construct may or may not be substantially cylindrical. Preferably, the extruded tube may include end walls with increased thickness compared to sidewalls. After extrusion of the tube, the desired surface features, such as the support bands, anti-expulsion portions, tool-engaging portions, and the mesh configuration, may be defined or cut into the implant using a laser techniques well known in the art or any other suitable method. It will be understood that mesh implants created from extruded tube may be formed faster and with less waste than conventional milling of implants from solid blocks. The extruded implant preferably has already formed therein the cavity for receipt of the bone growth material or osteogenic material. After extrusion and laser cutting of the desired surface features, the implant can be machined to prepare implants having the desired size for uses in a variety of ages of patients and bone structures.

The present invention contemplates modifications in the porous bone implant as would occur to those skilled in the art. It is also contemplated that processes embodied in the present invention can be altered, rearranged, substituted, deleted, duplicated, combined, or added to other processes as would occur to those skilled in the art without departing from the spirit of the present invention. In addition, the various stages, steps, procedures, techniques, phases, and operations within these processes may be altered, rearranged, substituted, deleted, duplicated, or combined as would occur to those skilled in the art. Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. An orthopedic implant comprising an impacted mesh body defining an interior chamber, said body comprising:
    a first end including a first support band extending about a first axis and defining a first opening into said interior chamber and defining a first end surface; and
    a second end opposite said first end and including a second support band extending about the first axis and defining a second opening into said interior chamber and defining a second end surface; and
    a longitudinal wall extending along a second axis substantially orthogonal to the first axis and between opposite transverse end walls, said longitudinal wall integral with said first and second support bands to define a one-piece, unitary body, said unitary body having a cross-sectional thickness measured orthogonal to the first axis at said first and second support bands that is greater than a cross-sectional thickness of said longitudinal wall, said longitudinal wall including an exterior surface extending between said first end surface and said second end surface, and wherein said first and second support bands provide the implant with an uninterrupted support band surface extending continuously about an outer perimeter of said first and second ends and flush with said exterior surface of said longitudinal wall and which does not extend beyond said exterior surface of said longitudinal wall in a direction orthogonal to the first axis, said longitudinal wall including a plurality of openings formed therethrough defining a grid pattern; and
    wherein said first end surface defined by said first support band and said second end surface defined by said second support band each comprise an arcuate end surface having a convex curvature extending along the second axis and between said opposite transverse end walls, said arcuate end surfaces of said first and second support bands defining a maximum height of the implant along the first axis positioned between said opposite transverse end walls that is greater than a height of a bone cavity to inhibit expulsion of the implant from the bone cavity.

2. The implant of claim 1 wherein the impacted, mesh body comprises a substantially rectangular prism body including a planar wall portion having a planar surface extending between said first end and said second end.

3. The implant of claim 2 wherein the longitudinal wall includes a first wall section having a first planar surface extending between said first end and said second end, and a second wall section having a second planar surface extending between said first end and said second end; and
    wherein said first and second planar surfaces are substantially parallel.

4. The implant of claim 1, wherein said first opening or said second opening is rectangular.

5. The implant of claim 1 wherein said plurality of openings define a plurality of equilateral or isosceles triangular openings.

6. The implant of claim 1 wherein said cross-sectional thickness of said longitudinal wall is selected to withstand impaction into a cavity between adjacent bone structures.

7. The implant of claim 1 wherein the longitudinal wall has an open area of at least about 50% based on the total exterior surface area of the longitudinal wall.

8. The implant of claim 1 wherein at least one of said opposite transverse end walls includes a tool engaging portion.

9. The implant of claim 3 wherein the at least one of said opposite transverse end walls includes a tool engaging portion.

10. An orthopedic implant comprising an impacted mesh body defining an interior chamber, said body comprising:
    a first end defining a first opening into said interior chamber and including a first support band extending about a first axis and positioned peripherally about said first opening and defining a first end surface, said first support band defining a lip or abutment projecting toward the interior chamber;
    a second end opposite said first end and defining a second opening into said interior chamber and including a second support band extending about the first axis and positioned peripherally about said second opening and defining a second end surface; and
    a longitudinal wall extending along a second axis substantially orthogonal to the first axis and between opposite transverse end walls and between said first and second ends, said longitudinal wall integral with said first and second support bands to define a one-piece, unitary body, said unitary body having a cross-sectional thickness measured orthogonal to the first axis at said first and second support bands that is greater than a cross-sectional thickness of said longitudinal wall, said longitudinal wall including an exterior surface extending between said first end surface and said second end surface, and wherein said first and second support bands provide the implant with an uninterrupted support band surface extending continuously about an outer perimeter of said first and second ends and flush with said exterior surface of said longitudinal wall and which does not extend beyond said exterior surface of said longitudinal wall in a direction orthogonal to the longitudinal first axis, said longitudinal wall including a plurality of openings formed therethrough defining a grid pattern, and wherein said unitary body exhibits a rectangular cross-sectional shape orthogonal to the first axis; and wherein said first end surface defined by said first support band and said second end surface defined by said second support band each comprise an arcuate end surface having a convex curvature extending along the second axis and between said opposite transverse end walls, said arcuate end surfaces of said first and second support bands defining a maximum height of the implant along the first axis positioned between said opposite transverse end walls that is greater than a height of a bone cavity to inhibit expulsion of the implant from the bone cavity.

11. The implant of claim 10 wherein the said first and second support bands each define a lip or abutment projecting toward the interior chamber.

12. The implant of claim 10 wherein the longitudinal wall includes a first wall section having a first planar surface extending between said first end and said second end, and a second wall section having a second planar surface extending between said first end and said second end.

13. The implant of claim 12 wherein said first and second planar surfaces are substantially parallel.

14. The implant of claim 12 comprising a tool engaging portion on at least one of said opposite transverse end walls.

15. The implant of claim 10 comprising an osteogenic material within the interior chamber.

16. An orthopedic implant defining an interior chamber, comprising:
   a first end including a first support band extending about a first axis and defining a first end surface;
   an opposite second end including a second support band extending about the first axis and defining a second end surface;
   a wall portion extending generally along a second axis substantially orthogonal to the first axis and extending between opposite transverse end walls and between said first end and said second end, said wall portion integral with said first and second support bands to define a one-piece, unitary body, said unitary body having a cross-sectional thickness measured orthogonal to the first axis at said first and second support bands that is greater than a cross-sectional thickness of said wall portion, said wall portion including an exterior surface extending between said first end surface and said second end surface, and wherein said first and second support bands provide the implant with an uninterrupted support band surface extending continuously about an outer perimeter of said first and second ends and flush with said exterior surface of said wall portion and which does not extend beyond said exterior surface of said wall portion in a direction orthogonal to the first axis, said wall portion defining a plurality of openings communicating with said interior chamber; and
   wherein said first end surface defined by said first support band and said second end surface defined by said second support band each comprise an arcuate end surface having a convex curvature extending along the second axis and between said opposite transverse end walls, said arcuate end surfaces of said first and second support bands defining a maximum height of the implant along the first axis positioned between said opposite transverse end walls that is greater than a height of a bone cavity to inhibit expulsion of the implant from the bone cavity.

17. The implant of claim 16 wherein at least one of said first and second ends defines an end opening communicating with said interior chamber.

18. The implant of claim 17 wherein said support band extends entirely about said end opening.

19. The implant of claim 16 wherein said plurality of openings in said wall portion define a grid pattern.

20. The implant of claim 16 wherein said plurality of openings in said wall portion are triangular-shaped.

21. The implant of claim 16 wherein said wall portion has a substantially rectangular cross-sectional configuration.

22. The implant of claim 16 wherein said wall portion includes a first planar wall section, and an opposite second planar wall section arranged substantially parallel with said first planar wall section.

23. The implant of claim 1 wherein said exterior surface of said longitudinal wall is substantially planar.

24. The implant of claim 10 wherein said exterior surface of said longitudinal wall comprises a substantially planar surface.

25. The implant of claim 17 wherein said exterior surface of said wall portion comprises a substantially planar surface.

26. The implant of claim 1 wherein said longitudinal wall includes a first longitudinal wall and an opposite second longitudinal wall, each of said first and second longitudinal walls defining said grid pattern and being planar.

27. The implant of claim 1 wherein each of said opposite transverse end walls includes a first bearing surface and an opposite second bearing surface, each of first and second bearing surfaces including a substantially planar surface defining one or more anti-expulsion features.

28. The implant of claim 27 wherein said anti-expulsion features comprise a plurality of teeth.

29. The implant of claim 10 wherein said longitudinal wall includes a first longitudinal wall and an opposite second longitudinal wall, each of said first and second longitudinal walls defining said grid pattern and being planar.

30. The implant of claim 10 wherein each of said opposite transverse end walls includes a first bearing surface and an opposite second bearing surface, each of first and second bearing surfaces including a substantially planar surface defining one or more anti-expulsion features.

31. The implant of claim 30 wherein said anti-expulsion features comprise a plurality of teeth.

32. The implant of claim 16 wherein said wall portion includes a first longitudinal wall and an opposite second longitudinal wall, each of said first and second longitudinal walls defining said plurality of openings and being planar.

33. The implant of claim 16 wherein each of said opposite transverse end walls includes a first bearing surface and an opposite second bearing surface, each of first and second bearing surfaces including a substantially planar surface defining one or more anti-expulsion features.

34. The implant of claim 33 wherein said anti-expulsion features comprise a plurality of teeth.

35. The implant of claim 1 wherein said convex curvature of said arcuate end surfaces extends continuously between said opposite transverse end walls.

36. The implant of claim 10 wherein said convex curvature of said arcuate end surfaces extends continuously between said opposite transverse end walls.

37. The implant of claim 16 wherein said convex curvature of said arcuate end surfaces extends continuously between said opposite transverse end walls.

* * * * *